United States Patent
Stout, Jr.

(10) Patent No.: US 6,926,441 B2
(45) Date of Patent: Aug. 9, 2005

(54) PORTABLE X-RAY TABLE

(76) Inventor: Fred T. Stout, Jr., 8705 Sanctuary Dr., Kirtland Hills, OH (US) 44060

( * ) Notice: Subject to any disclaimer, the term of this patent is extended or adjusted under 35 U.S.C. 154(b) by 64 days.

(21) Appl. No.: 10/419,528

(22) Filed: Apr. 21, 2003

(65) Prior Publication Data
US 2004/0208291 A1 Oct. 21, 2004

(51) Int. Cl.$^7$ ............................................. G03B 42/02
(52) U.S. Cl. ........................ 378/177; 378/181; 378/209; 5/601
(58) Field of Search ................................. 378/167, 177, 378/181, 182, 189, 196, 197, 204, 208, 209; 5/81.1 HS, 86.1, 601, 621

(56) References Cited

U.S. PATENT DOCUMENTS

| | | | | |
|---|---|---|---|---|
| 2,989,634 A | | 6/1961 | Ould et al. ..................... 250/58 |
| 3,648,305 A | | 3/1972 | Ersek ................................. 5/82 |
| 3,774,045 A | | 11/1973 | Trott ........................... 250/444 |
| 3,967,126 A | | 6/1976 | Otto, Jr. ...................... 250/439 |
| 4,097,748 A | * | 6/1978 | Monvoisin ................... 378/146 |
| 4,103,170 A | | 7/1978 | Spradlin ....................... 250/451 |
| 5,016,268 A | * | 5/1991 | Lotman ........................ 378/177 |
| 5,138,646 A | * | 8/1992 | Hubert et al. ................ 378/177 |
| 5,190,056 A | | 3/1993 | Hull ............................. 128/870 |
| 5,222,115 A | * | 6/1993 | Highgenboten .............. 378/177 |
| 5,422,928 A | * | 6/1995 | Payne .......................... 378/177 |
| 6,163,902 A | | 12/2000 | Mollette et al. ................ 5/601 |
| 6,266,831 B1 | * | 7/2001 | Heimbrock ...................... 5/601 |
| 6,459,923 B1 | * | 10/2002 | Plewes et al. .............. 600/411 |
| 6,823,037 B2 | * | 11/2004 | Riemer et al. ................. 378/15 |
| 2003/0021384 A1 | * | 1/2003 | Ohkoda ....................... 378/177 |

* cited by examiner

*Primary Examiner*—Allen C. Ho
(74) *Attorney, Agent, or Firm*—James A. Lucas; Driggs, Lucas, Brubaker & Hogg Co., LPA

(57) ABSTRACT

An articulated x-ray table comprises a planar, rigid radiolucent top support and a base spaced therefrom to form a gap whereby radiographic plates can be inserted and withdrawn. The gap is maintained by the use of one or more trolleys that are moveable along the length of the table to be moved into proximity to the location where the plate is to be inserted. Generally, two of the trolleys are used along either side of the table for placement near the x-ray plate. The trolleys move in grooves or tracks on the edges of the base along the length of the table. Each trolley includes wheels that engage the grooves, and a separate roller that engages the top support. This permits the trolleys to be easily moved along the guide notwithstanding the weight of a patient on the table. The table can be used for animals and humans.

20 Claims, 6 Drawing Sheets

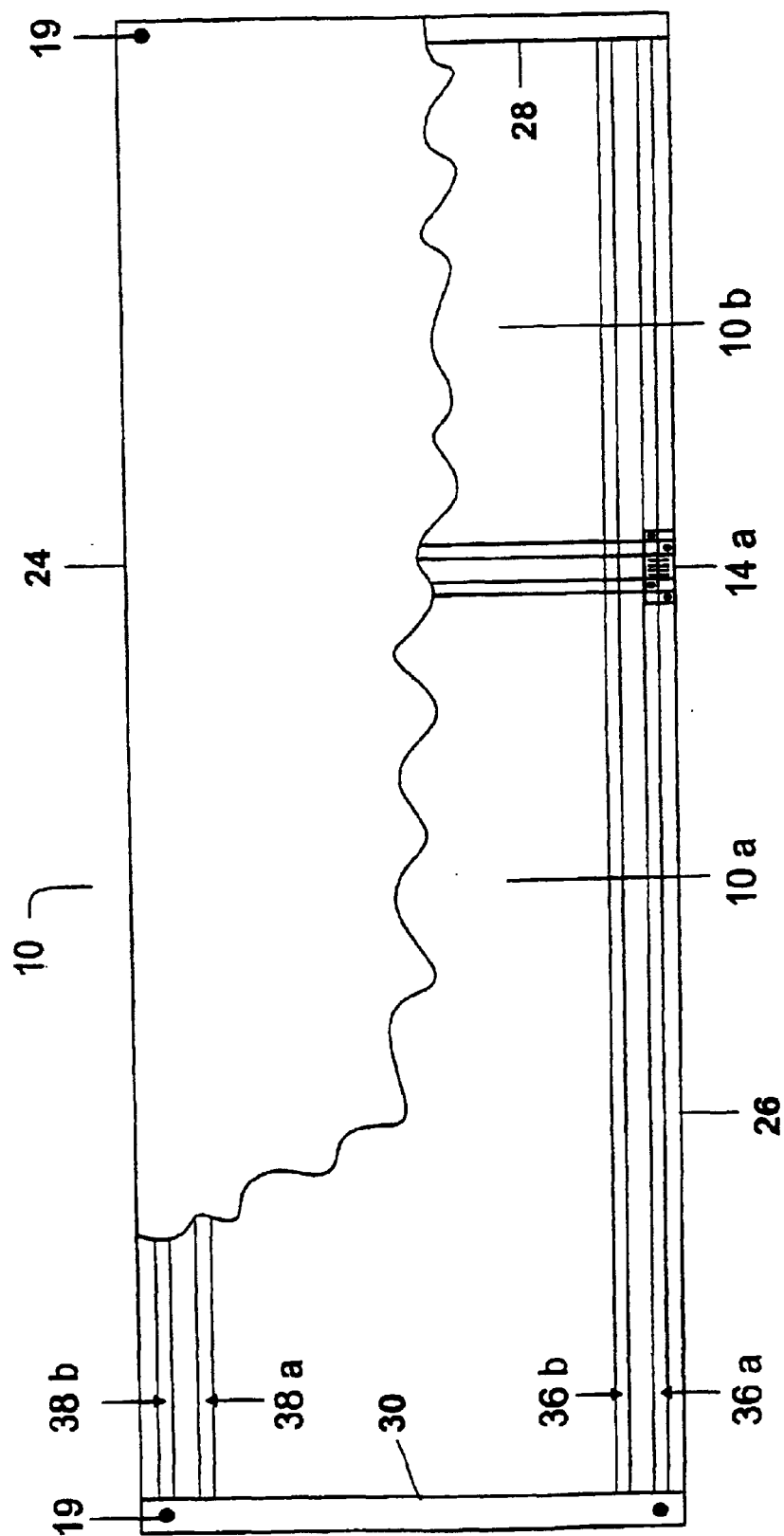
Fig: 1

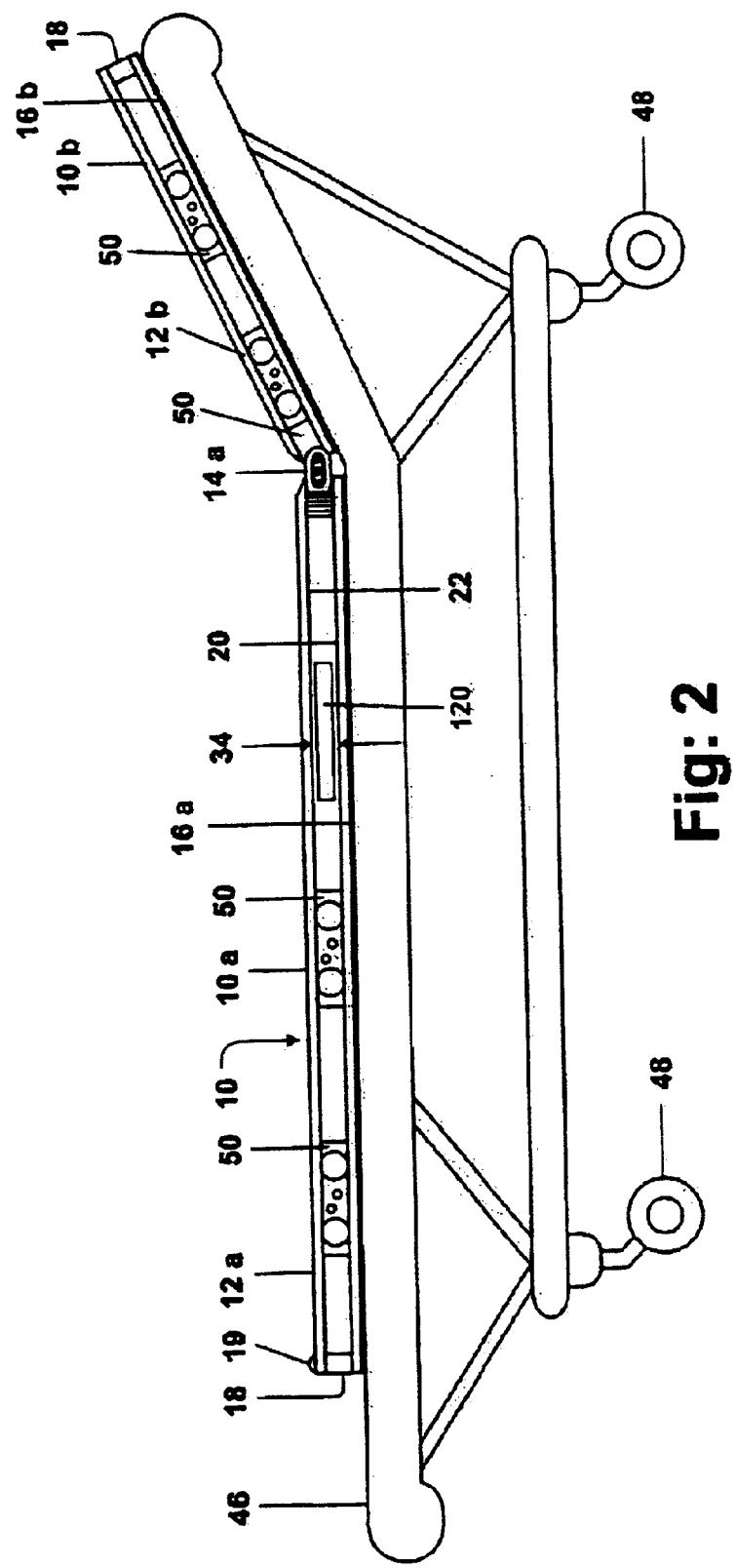
Fig: 2

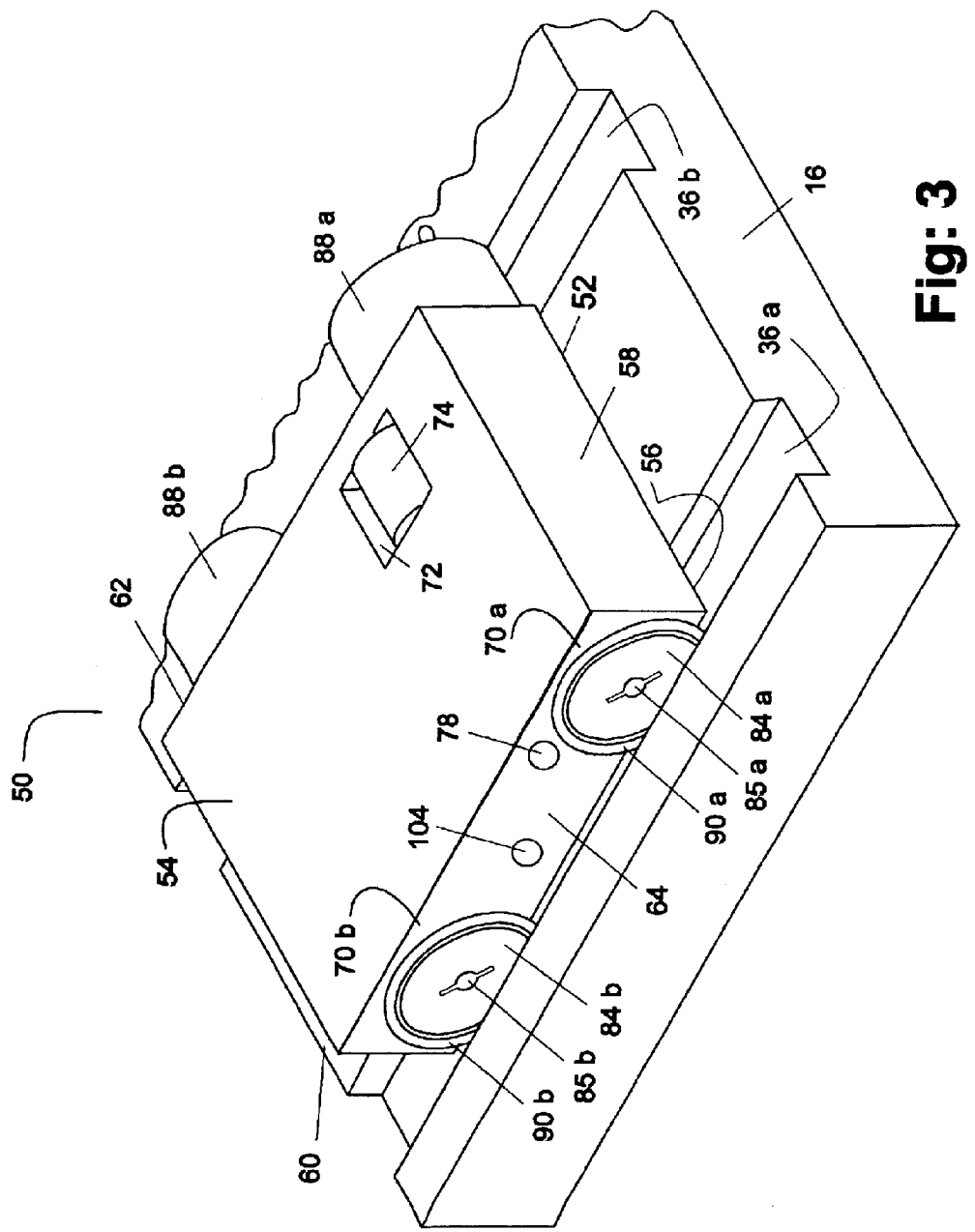
Fig: 3

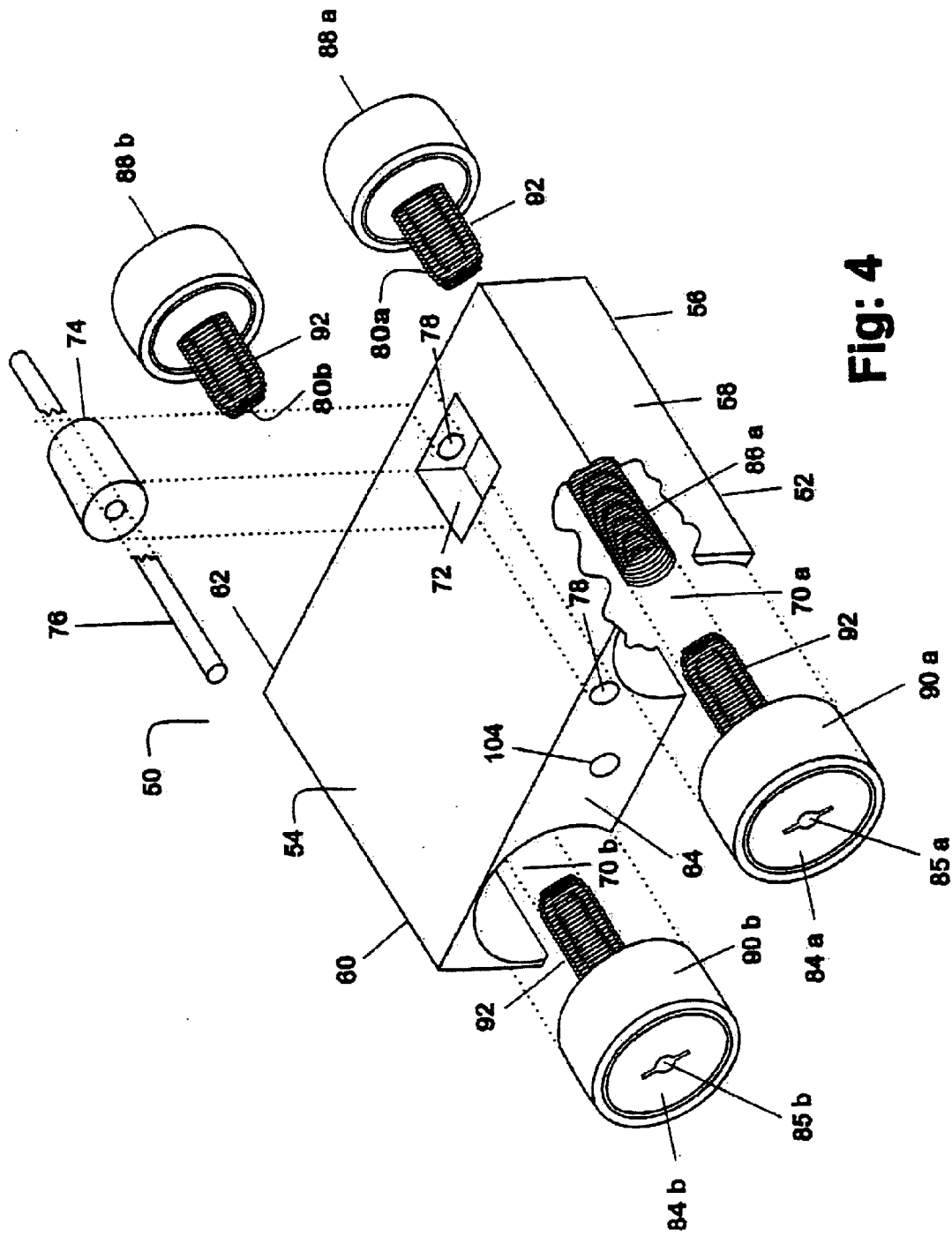
Fig: 4

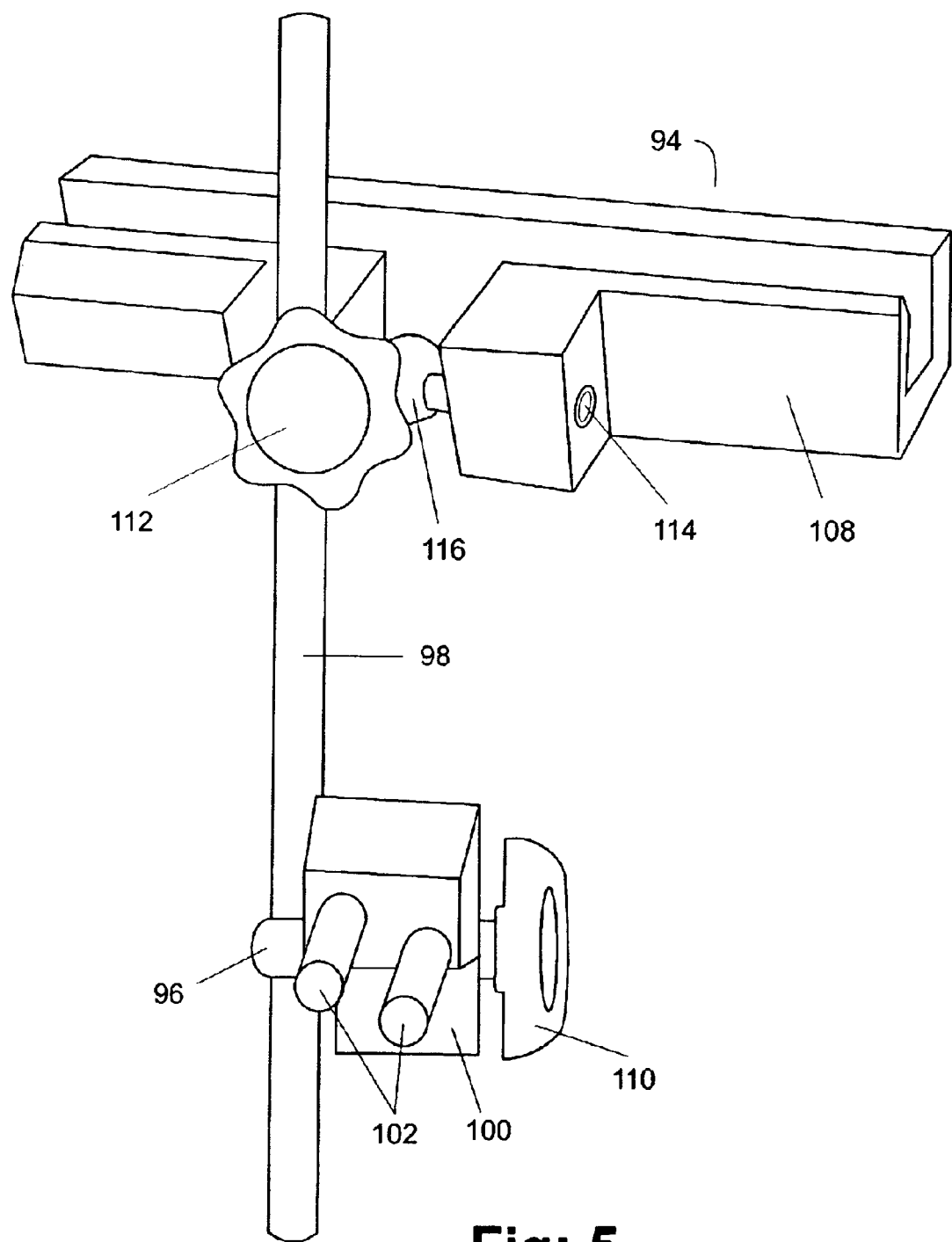
Fig: 5

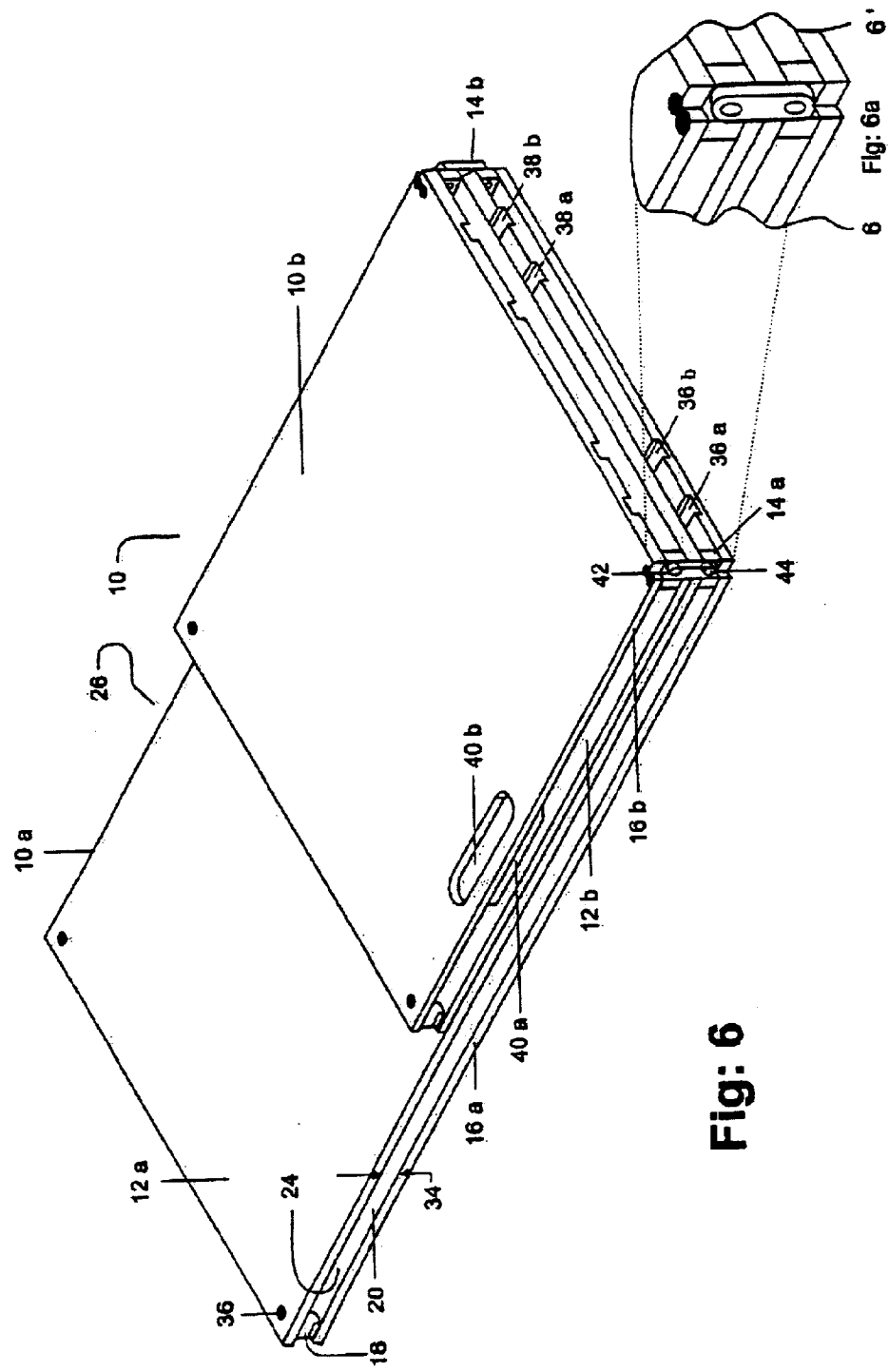

PORTABLE X-RAY TABLE

FIELD OF THE INVENTION

This invention relates generally to the field of boards or tables for supporting the human body, or that of an animal, while allowing for x-rays or other radio-images to be taken of the patient.

BACKGROUND OF THE INVENTION

X-ray examinations are often a first step in the treatment of persons or animals that have undergone trauma that possibly has resulted in one or more broken or displaced bones. It is well known to those in the medical profession that an emergency room patient is often moved to an x-ray table for such an examination, after which the patient is then again moved from the table to another location for the next step of diagnosis or treatment. Even if the patient is not transferred from table to table, the patient must often be turned, or otherwise moved, to permit an x-ray plate to be positioned at the right location for the x-ray to be taken. When the x-ray plate must be placed beneath the patient for examination, this requires lifting of the patient, or at least a portion of the patient. Such movement of a patient can be painful, harmful or even fatal.

Various prior art devices have attempted to meet the need for an x-ray table that allows for placement of an x-ray plate at any location beneath a patient without the need for moving the patient. Some of these devices comprise an upper frame holding a rigid translucent panel and a lower frame separated from the upper frame by channels or slots that allow for insertion and removal of the x-ray plate. In most instances, the two frames are separated by a plurality of fixed supports that determine where the x-ray plate can be positioned for picture taking. If these locations do not coincide with the precise area of the patient that requires the x-ray, some manipulation of the patient's body may be found to be necessary. Attendant with this is the possibility of further injury to the patient as previously noted.

BRIEF SUMMARY OF THE INVENTION

It is an object of the present invention to provide a portable table on which a patient can be placed for the taking of one or more x-rays without unnecessary movement of the patient's body.

A further object of the invention is to provide such a table with open sides such that that an x-ray plate may be positioned at any location beneath the patient to attain the best positioning for x-rays to be taken.

These and other objects and advantages that will become apparent upon a reading of following description are achieved in the manner to be hereinafter described as follows.

The invention relates to an x-ray table that comprises a top planar support made from a substantially radiolucent material and is adapted to receive the body of a patient. A rigid planar base is parallel to the top support and is spaced therefrom to form a slot or gap adapted to receive an x-ray plate. At least one trolley is positioned between the top support and the base, and is moveable therebetween. The base is equipped with means, such as wheels, rollers or slides, that permit the trolley to be easily rolled or slid into proximity of the location where the x-ray plate is to be inserted. The trolley serves to maintain adequate spacing between the base and the top support. This allows the plate to be freely inserted and withdrawn without the weight of the patient compressing the gap between the top support and the base. The support and the base typically are rectangular in shape, defining two generally parallel opposed sides, a head and a foot. The base includes a guide along at least one of the opposed sides, in the form of one or more, preferably two, grooves that define a path along which the trolley rolls or slides.

The invention also relates to a moveable trolley for use with an x-ray table. The trolley comprises a body having a top and a bottom defining the thickness thereof. The thickness of the body corresponds generally to the thickness of an x-ray plate used with the table. Two or more guide wheels, rollers or slides are rotatably mounted on the bottom of the body. Their axis of rotation is parallel to the top and bottom of the body. These wheels or slides are adapted to engage and move along a guide located at each side edge of the x-ray table. The trolley includes at least one additional wheel or roller parallel to the guide wheels. This third wheel or roller has a periphery that extends a slight distance above the top of the block, whereby the distance between the bottom of the block and periphery of the wheel extending above the block is typically greater than the thickness of the x-ray plate usable with the x-ray table. The trolley body includes an outboard side and an inboard side. The portion of the guide wheels along the outboard side of the trolley body is generally flush with the outboard side of the body. The portion of the guide wheels along the inboard side thereof is mounted whereby at least a portion of the wheels extend axially beyond the inboard side.

The invention also relates to the method of making the x-ray table and trolley, and the method of employing them for their intended uses.

BRIEF DESCRIPTION OF THE DRAWINGS

FIG. 1 is a top view of the x-ray table of the present invention, partially cut away and shown in the open position;

FIG. 2 is an elevational view of the x-ray table resting on a gurney;

FIG. 3 shows the trolley assembly;

FIG. 4 is an exploded perspective view of the trolley of FIG. 3;

FIG. 5 shows a variation of the x-ray table with a side mounted plate holder;

FIG. 6 is a perspective view of the table folded into the carrying position; and FIG. 6a is an enlarged corner view of the table of FIG. 6.

DETAILED DESRIPTION OF THE INVENTION

Turning now to FIGS. 1 and 2, an x-ray table 10 of the present invention is shown, composed of a larger section 10a and a smaller section 10b joined to one another by strap hinges 14a and 14b. Each portion 10a, 10b comprises a top support 12a, 12b of a flat, rigid material that preferably is radiolucent and a base 16a, 16b. By radiolucent is meant that the material is easily penetrated by x-rays, while at the same time being substantially visually transparent.

The two portions of the top support 12a, 12b are sufficiently rigid, preferably, to permit medical personnel to perform resuscitation or other lifesaving techniques on a patient lying on the table 10. Typically, the top support is constructed of a transparent plastic, such as Plexiglas® acrylic plastic or Lexan® polycarbonate, or a material such as acrylonitrile butadiene-styrene or acrylic polyvinylchloride, and is sufficiently thick so that it maintains rigidity under the weight of a patient's body. Typically, the first section 12a is approximately two feet wide and four feet long and serves to support the torso of a patient. The second section 12b is about two feet square and would normally support the upper body and head of the patient. Obviously, these dimensions might be different for an x-ray table that is used by a veterinarian for the examination of animals. The top support may be covered with a radiolucent foam material, such as expanded ABS, for the comfort of the patient. Alternatively, it can be covered with a layer of one or more gel packs or pads to provide comfortable support for the patient.

The top support and the base are joined to one another by washers 18 at each corner. The washers are dimensioned so that the gap or space 34 between the top surface 20 of the base 16 and the lower surface 22 of the top support 12a, 12b is slightly wider than the thickness of a standard x-ray plate. A bolt 19 passes through each washer and through the top support and base, and is secured with a nut (not shown) on the underside of the table 10. The assembled table 10 includes two parallel opposing sides 24, 26, a head 28 and a foot 30. Each side contains guide means preferably in the form of a pair of grooves 36a, 36b and 38a, 38b along the length of both sections 16a, 16b of the base.

The strap hinges 14a, 14b allow the two portions of the table 10a, 10b to be folded into a compact carrying position for ease of transport. Openings (40a, 40b in FIG. 6) are positioned in the two portions (10a, 10b) of the top support so that the openings meet to form a carrying handle when the table is folded. The openings preferably are positioned along the side so that the table is balanced when folded for ease of carrying. Although not shown, the table can include a suitable latch to keep the two portions together when folded for transport or storage. The two washers 18 facing the edges of the table are provided with notches 42a, 42b and pins 44, as shown in FIG. 6, over which the hinges 14a, 14b are pivotally joined.

The table 10 is shown in FIG. 2 resting on a typical hospital gurney 46 mounted on rollers 48 for mobility. The table includes four trolleys 50, two each on the larger portion 10a and the smaller portion 10b of the table. As shown, the upper portion has been pivoted into an elevated position to support the upper torso of a patient at an acute angle from horizontal. These trolleys 50 are used as spacers between the top supports 12a, 12b and the base 16a, 16b. An x-ray plate 120 is positioned between the two trolleys 50 in the space between the top support 12a and the base 16a.

Turning now to FIGS. 3 and 4, the details of the trolley and its component parts are shown. The trolley 50 consists of a body 52. The body comprises a top surface 54, a bottom surface 56, two ends 58, 60, an inboard side 62, and an outboard side 64. Two wheel wells 70a, 70b extend into the body 52 from the bottom surface 56, terminating near the top surface 54. A rectangular hole 72 extends vertically into the body 52 from the top surface 54. A small roller 74 is mounted in the hole 72 on a pin 76 press fitted into hole 78. The periphery of the roller 74 extends slightly (e.g. ⅛" to ¼") above the top surface 54 and is adapted to ride on the underside of the top support. The trolley 50 includes four wheels or rollers that move in low friction ball bearings, two of the wheels 88a, 88b on the inboard side and two more 90a, 90b on the outboard side. The inboard wheels 88a, 88b are rotatably mounted on stub axles 80a, 80b that are threaded into corresponding holes, one of which is shown as 86a in FIG. 4, extending axially into the body of the trolley. These inboard wheels extend axially beyond the inboard side of the body. The outboard wheels 90a, 90b are likewise rotatably mounted on stub axles 84a, 84b having threads 92 that are threaded into threaded holes (one of which is shown as 86a in FIG. 4) tapped into the body 52 in the same axial plane as the corresponding holes 82a, 82b on the inboard side of the body. Slots 85a, 85b permit the stub axles to be threaded into and out of the threaded holes using a screwdriver or the like. The trolley 50 is shown in FIG. 4 filly assembled and mounted with the wheels 88a, 88b and 90a, 90b rolling in guide tracks or grooves 36a, 36b in the base 16.

Turning now to FIG. 5, there is shown an attachment 94 that rides on a trolley and that allows for the positioning of an x-ray plate at virtually any angle along the side of a patient for lateral views of the torso, head or shoulders. The device comprises a tray 108 having a pin 114 extending through the base 116 of knob 112 connected and tightened to a rod 98 using the knob 112. This rod, in turn, is secured through a coupler 96 to a bracket 100 by a second threaded knob 110. The bracket 100 contains a pair of dowel pins 102 that engage two holes 78, 104 shown in FIG. 3 and in the outboard side 64 of the trolley 50. Although the attachment 94 is shown with one of the dowel pins engaging the same hole 78 into which pin 76 is pressed to hold the small wheel 74, it should be understood that the trolley can have one hole for the pin 76 and two separate holes to receive the dowel pins 102.

Typically, a total of four trolleys are used at one time to maintain the spacing between the top support and the base for a single x-ray plate. Two of the trolleys are positioned in the grooves on the inboard side of the table and two are placed on the outboard grooves opposite the two on the inboard side.

The smaller portion of the x-ray table is adapted for use in taking x-rays of the upper portion of the human body, including head, neck, shoulder and upper spine. In use, there may be a need for the upper body to lie against the upper portion at an acute angle to the normal horizontal position (see FIG. 2). Typically, the angle will be adjusted by elevating or lowering a portion of the gurney or bed on which the x-ray table rests. When the table is not horizontal, suitable stops may be needed to prevent the trolleys from rolling or sliding down along the grooves after the trolleys are positioned at the location for the x-rays to be taken. This can be achieved by providing a brake or a locking device for the wheels to prevent their rotation. Another way is to clamp a rod or bar across the width of the base or across each set of grooves to prevent the trolleys from rolling or sliding downhill under the pull of gravity.

While the invention has been described in combination with specific embodiments thereof, there are many alternatives, modifications, and variations that are likewise deemed to be within the scope thereof. Accordingly, the invention is intended to embrace all such alternatives, modifications and variations as fall within the spirit and scope of the appended claims. Therefore, it should be understood that the trolley 50 can be moved in the guide tracks manually. The trolley can include a handle to facilitate the manual movement of the trolley along the length of the table. The handle can, for example, be threaded into a tapped hole on the outboard side of the trolley. The trolley can be provided with a powered means, such as a small servo motor, to power the wheels to move the trolley back and forth along the guide track. These motors can be hand wired or controlled by remote control, such as by a radio frequency transmitter or the like. Of course, care must be taken to provide the necessary shielding to prevent the motor from interfering with the x-rays.

The body and the rollers used in the trolley can be made of any suitable material that has the requisite strength to withstand the weight being placed on the x-ray table by the patient being examined. It should likewise be made from a material that can easily be cleaned and disinfected as needed. Stainless steel is a preferred material for the construction of the body, the rollers, stub axles and other components in the trolley. Non-metallic moldable polymeric materials, such as Delrin®, Nylon® and Teflon® may also be considered for use for some or all of the component parts of the trolley. The rollers can be equipped with permanently lubricated and sealed bearings to further simplify sterilization.

In yet another alternative, the wheels or rollers can be replaced with low friction slides which can be readily slid along the grooves or tracks provided for them.

Other variations can be incorporated into the design and construction of the trolley without departing from the present invention. For example, the trolley is described as having one top roller. However, it should be understood that two or more rollers, placed side by side, or with one in back and one in front, can also be used. As with the bottom wheels, the top roller can be replaced with one or more low friction slides that contact the bottom surface of the top support to permit the trolley to be readily slid into position along the guide track into proximity to the location where the x-ray will be taken. Instead of using stub axles for the bottom wheels, one piece shafts can extend completely through the body of the trolley with the guide rollers mounted on both the inboard and the outboard ends of the shaft Although the table is shown with two sections hinged to one another to allow for a more compact unit for portability, it should also be understood that it can be fabricated with a one piece top support and one piece base joined to one another in the same manner as previously described in connection with the articulated structure shown in FIGS. 1 and 2. Furthermore, it should also be understood that the two sections may be hinged together in such a manner that they will open through a 180° arc but not beyond. It should further be understood that the table is useful with other types of radio imaging equipment, not being limited solely to x-ray machines.

What is claimed is:

1. An x-ray table comprising:
   a) a substantially top planar support adapted to receive the body of a patient;
   b) a base parallel to the top support and spaced therefrom to form a slot there between, said slot adapted to receive an x-ray plate; and
   c) at least one trolley between the top support and the base and moveable on rollers from one location to another there between to permit the positioning of the trolley in proximity of an x-ray plate to maintain a given spacing between the top support and the base.

2. The x-ray table according to claim 1 wherein the top support is made from a substantially radiolucent material.

3. The x-ray table according to claim 1 wherein the at least one trolley serves as a spacer between the top support and the base to allow the x-ray plate to be freely inserted and withdrawn without binding under the weight of the patient.

4. The table according to claim 1 wherein the top support and the base are defined by opposed sides, and the base includes a guide along at least one of the opposed sides to define a path along which the trolley moves.

5. The table according to claim 4 wherein the guide comprises two parallel grooves along which the trolley moves.

6. The table according to claim 1 wherein said trolley comprises:
   a) a body having a top and a bottom defining the thickness thereof that corresponds generally to the thickness of an x-ray plate;
   b) guide wheels rotatably mounted on the body and having an axis of rotation parallel to the top and bottom thereof, said guide wheels engaging and moveable along a guide included in the base of the x-ray table;
   c) at least one additional wheel parallel to the guide wheels, having a periphery extending a slight distance above the top of the block contacting the top support, thereby maintaining the slot spacing that is greater than the thickness of x-ray plate usable with the x-ray table.

7. The table according to claim 6 wherein the body of the trolley includes an outboard side and an inboard side, at least two of the guide wheels located along the outboard side of the trolley body generally flush therewith.

8. The table according to claim 7 including at least two guide wheels along the inboard side of the trolley.

9. The table according to claim 8 wherein the at least two guide wheels along the inboard side of the trolley are mounted so that at least a portion of the wheels extend axially beyond the inboard side of the trolley.

10. A moveable trolley adapted for use as a spacer with an x-ray table having a top support and a base spaced therefrom to accept an x-ray plate, said trolley comprising:
    a) a body having a top and a bottom defining the thickness thereof corresponding generally to the thickness of an x-ray plate useful with the table;
    b) guide wheels rotatably mounted to the body, said guide wheels adapted to engage and move along a guide in the x-ray table;
    c) at least one additional wheel axially parallel to the guide wheels and having a periphery extending a slight distance above the top of the body, whereby the trolley can serve as a spacer between the top support and the base of the x-ray table.

11. The trolley according to claim 10 wherein the body includes an outboard side and an inboard side, the outboard side having at least two guide wheels along the outboard side of the trolley body adapted to move along the guide located along an edge of the x-ray table.

12. The trolley according to claim 11 wherein said at least two guide wheels are generally flush with the outboard side of the trolley body.

13. The trolley according to claim 11 including at least two guide wheels along the inboard side thereof.

14. The trolley according to claim 13 wherein the at least two guide wheels along the inboard side of the body are mounted whereby at least a portion of the wheels extend axially beyond the inboard side.

15. The trolley according to claim 14 wherein the top and the bottom of the body are parallel to one another and the guide wheels have an axis of rotation parallel to said top and bottom.

16. The trolley according to claim 10 further including an articulated arm coupled to the body on the outboard side thereof, said arm being adjusted in all planes and including a holder for an x-ray plate useful for taking exposures laterally along the side of a patient lying on an x-ray table.

17. A method of positioning an x-ray plate beneath a portion of the body of a patient on an x-ray table comprising the steps of:
    a) forming the table from a rigid top support and a rigid base, spaced apart to form a slot normally wide enough to receive the x-ray plate, said table having a head, a foot and two opposed parallel sides;

b) providing guide means along the two parallel sides between the head and the foot;

c) placing one or more trolleys in each of the guide means and positioning each trolley at a location in proximity to the x-ray plate;

d) moving each trolley on guide wheels in two parallel grooves forming each of the guide means from one location to another along the guide means, thereby defining the location where the x-ray plate will be used; and e) using at least one additional wheel parallel to the guide wheels, said additional wheel having a periphery extending a slight distance above the to of the trolley whereby the space occupied by the trolley is greater than the thickness of the x-ray plate usable with the x-ray table.

18. The method according to claim 17 including fabricating each trolley to have a body having a top and a bottom parallel to one another, thereby defining the thickness thereof, and corresponding generally to the thickness of an x-ray plate used with the table; and rotatably mounting the guide wheels to the body so that the wheels have an axis of rotation parallel to the top and bottom thereof, said guide wheels engaging a guide means in the x-ray table.

19. The method according to claim 18 wherein the body of the trolley includes an outboard side and an inboard side, and the outboard side engages and rolls along the guide located on a side of the x-ray table on at least two guide wheels mounted along the outboard side of the trolley body and generally flush with the outboard side.

20. The method according to claim 19 wherein the trolley also rolls on at least two guide wheels along the inboard side of the body, at least a portion of the wheels extending axially beyond the inboard side of the trolley.

* * * * *